United States Patent [19]

Tentorio et al.

[11] Patent Number: 5,162,309

[45] Date of Patent: Nov. 10, 1992

[54] MONO (2-AMMONIUM-2-HYDROXYMETHYL-1,3-PROPANEDIOL)(2R,CIS)-1,2-EP-OXIPROPYL-PHOSPHONATE WITH IMPROVED CHARACTERISTICS OF STABILITY AND PROCESSING

[75] Inventors: Dario Tentorio, Viganó ; Graziano Castaldi, Briona; Claudio Giordano, Monza; Franco Pozzi, Como, all of Italy

[73] Assignee: Zambon Group, Vincenza, Italy

[21] Appl. No.: 557,030

[22] Filed: Jul. 25, 1990

[30] Foreign Application Priority Data

Jul. 27, 1989 [IT] Italy ............... 21340 A/89

[51] Int. Cl.⁵ ............... A61K 31/665; C07F 9/38
[52] U.S. Cl. ............... 514/99; 514/475; 549/217; 549/551; 549/554
[58] Field of Search ............... 549/217, 551, 554; 514/99, 475

[56] References Cited

U.S. PATENT DOCUMENTS

| | | | |
|---|---|---|---|
| 3,641,063 | 2/1972 | Miller | 260/348 R |
| 3,914,231 | 10/1975 | Hendlin et al. | 544/374 |
| 4,727,065 | 2/1988 | Chiarino et al. | 514/99 |
| 4,863,908 | 9/1989 | Chiarino et al. | 514/76 |

FOREIGN PATENT DOCUMENTS

| | | |
|---|---|---|
| 0027597 | 4/1981 | European Pat. Off. . |
| 511527 | 7/1983 | Spain . |
| 2025975 | 1/1980 | United Kingdom . |
| 2062640 | 5/1981 | United Kingdom . |

*Primary Examiner*—C. Warren Ivy
*Assistant Examiner*—Ba K. Trinh
*Attorney, Agent, or Firm*—Stevens, Davis, Miller & Mosher

[57] ABSTRACT

A process is described for the preparation of mono (2-ammonium-2-hydroxymethyl-1,3-propanediol) (2R,cis)-1,2-epoxypropyl-phosphonate with improved characteristics of stability, of processing for the preparation of pharmaceutical forms and of stability of the pharmaceutical forms that contain it.

6 Claims, No Drawings

MONO (2-AMMONIUM-2-HYDROXYMETHYL-1,3-PROPANEDIOL)(2R,CIS)-1,2-EP-OXIPROPYL-PHOSPHONATE WITH IMPROVED CHARACTERISTICS OF STABILITY AND PROCESSING

The present invention concerns the compound mono (2-ammonium-2-hydroxymethyl-1,3-propanediol)(2R-,cis)-1,2-epoxypropyl-phosphonate with new physico-chemical characteristics, the process for its preparation and pharmaceutical compositions that contain it as an active ingredient.

The above mentioned compound (hereinafter indicated as FT) is the mono salt of trihydroxymethyl-aminomethane (THAM) with (2R,cis)-1,2-epoxypropyl-phosphonic acid, a compound endowed antibiotic activity known as Fosfomycin (Merck Index, X Edition, page 607, no. 4137).

The compound FT of formula

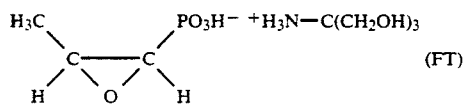 (FT)

was described for the first time in European patent No. 0 027 597 (Zambon S.p.A.), was developed for the monodose treatment of urinary tract infections and is commercialized in Italy with the trade mark "Monuril" which distinguish a pharmaceutical form in water soluble granulate.

The process for the preparation of FT described in the European patent No. 0 027 597 consists in reacting bis-(2-ammonium-2-hydroxymethyl-1,3-propanediol) (2R-cis)-1,2-epoxypropyl-phosphonate (i.e. the bis-salt of THAM with Fosfomycin) with p.toluenesulfonic acid in ethanol.

The bis-salt of THAM with Fosfomycin was described in British patent No. 2 025 975 or in U.S. Pat. No. 4,727,065 both in the name of Zambon S.p.A.

The compound FT prepared according to European patent No. 0 027 597 shows the following characteristics (see example 2):

melting point: 114°-116° C. (113-116)
pH: 3.77 (3.6-3.8)
surface area: 1.72 m²/g (1.0-2.9).

The above reported values are those of a sample selected as standard (Reference A) and the values between brackets show the minimum and maximum variations of the parameters within 5 identical preparations.

Spanish patent No. 511,527 (Compania Espanola de la Penecilina y Antibioticos S.A.) specifically concerns a process of the preparation of the mono-salt of THAM with Fosfomycin (FT) as well as of the bis-salt of THAM with Fosfomycin.

Said process for the preparation of FT consists in reacting in an alcoholic medium the mono-salt of (+)-alpha-phenethylamine of Fosfomycin with THAM and sulphonic acid in the molar ratio 1:1:1. When the bis-salt of THAM with Fosfomycin is desired the three above said compounds are use din the ratio 1:2:1. Compound FT prepared according to Spanish patent No. 511,527 shows the following characteristics (see example 3):

melting point: 120°-122° C. (118-122)
pH: 3.8 (3.7-3.9)
surface area: 0.88 m²/g (0.85-1.25).

The above reported values are those of a sample selected as standard (Reference B) and the values between brackets indicate the minimun and maximum variations of the parameters with 5 identical preparations.

U.S. Pat. Nos. 3,641,063 and No. 3,914,231 in the name of Merck describe Fosfomycin and its salts as well as the purification of the product obtained by fermentation processes.

In example 7 of U.S. Pat. No. 3,641,063 and in example 11 of U.S. Pat. No. 3,914,231, which are identical to each other, a process for the purification of the sodium salt of Fosfomycin carried out by three subsequent chromatographic purifications is described.

In the first one, the sodium salt of Fosfomycin is eluted on an ion-exchange resin by means of a buffer consisting of an aqueous THAM solution.

We have verified that the elute from this chromatographic column contains THAM and Fosfomycin in the weight ratio 350:1 and, by means of mass-spectroscopy, we have verified that in the mixture no FT is present.

Accordingly, if it was desired to prepare FT before the present invention, it was possible to use the process described in European patent No. 0 027 597 which affords FT having the characteristic of the above reported reference A or to use the process described in Spanish patent No. 511,527 which affords FT having the characteristics of the above reported Ref. B.

Fosfomycin exhibits relatively little stability mainly due to the easy opening of the epoxide, and it is sensitive to both humidity and temperature.

This instability stands also for the mono-salt with THAM both prepared according to European patent No. 0 027 597 (Ref. A) and according to Spanish patent No. 511,527 (Ref. B) thus making necessary to use burdensome precautionary measures for the storage of the active ingredient (sealed containers with driers), for its processing into finished pharmaceutical forms (operations carried out in controlled environments with R.H. lower than 25%) as well as for the stability of the finished pharmaceutical forms. This is particularly true for solid pharmaceutical forms such as "Monuril" the stability of which as granulate is limited to two years.

We have now surprisingly found a new process for the preparation of FT which affords the product with physico-chemical characteristics different from those of FT obtained by previously known methods and with improved characteristics of stability which allow for better storage of the active ingredient, an easier processing of the substance for preparing pharmaceutical forms and an improved stability of the granulate prepared from it.

The new process, which is one of the objects of the present invention, consists in preparing in a reactor at a temperature comprised between 15° and 50° C. a methanolic solution of bis-(2-ammonium-2-hydroxymethyl-1,3-propanediol)(2R,cis)-1,2-epoxypropylphosphonate (i.e. the bis-salt of THAM with Fosfomycin), an equimolecular amount of methanesulphonic acid, an equimolecular amount of mono (+)-alpha-phenethylammonium (2R,cis)-1,2-epoxypropyl-phosphonate (i.e. the mono salt of phenethylamine with Fosfomycin) and an amount of 2–3% in mols, with respect to the amount of THAM contained in the bis-salt of THAM with Fosfomycin of trihydroxymethyl-aminomethane (THAM), the solution is then diluted with ethanol in amounts between 4:1 and 10:1 with respect to the volume of the solution, and cooled at about 0° C. under a slow stirring characterized by the following parameters:

length of the anchor stirrer/diameter of the reactor higher than 0.7 specific power lower than 0.25 kw/m$^3$.

The precipitate consisting of the desired product is collected. The crystallization is preferably seeded by adding a smaller amount of FT.

The yield is about 75% in pure FT.

The mother liquors can be reused as such or from them the bis-salt of THAM with Fosfomycin may be recovered by adding an equimolecular amount of THAM with respect to the non-precipitated FT. The thus obtained bis-salt is reused. The above described process affords FT, which is an object of the present invention, having the following characteristics:

melting point: 122°-124° C.

pH: comprised between 4.0 and 5.0 surface area: comprised between 0.2 and 0.5 m$^2$/g.

Hereinafter we will indicate as FT* the product obtained by the above described process and having the above reported characteristics, in order to distinguish it from the general abbreviation FT and from FT prepared by the process described in European patent No. 0 027 597 (Ref. A) or by that of the Spanish patent No. 511,527 (Ref. B).

The process for the preparation of FT* is reproducible and easily industrially carried out thus providing FT* in good yields and high purity with the above reported chemical and physical characteristics are reproducible and remain always in the above values.

FT* with said characteristics is more stable than FT according to Ref. A and Ref. B (see example 4) both with respect to humidity and temperature and consequently can be stored in conditions not burdensome from an industrial point of view.

Thanks to the characteristics of FT* it is possible to prepare pharmaceutical forms in granulate under more simple and less burdensome processing conditions (see example 5).

The pharmaceutical compositions thus obtained, which are another object of the present invention, result to be more stable (see example 6) and allow to increase the expiry date of the pharmaceutical composition up to three years from its preparation, while a two years stability characterizes the granulate containing FT according to Ref. A presently commercialized.

Thus, the new above described process allows to obtain a product (FT*) having different chemical and physical characteristics endowed with improved stability which allow a more simple and convenient storage of the active ingredient, with improved characteristics for its processing which allow a more simple and convenient preparation of solid pharmaceutical forms, in particular granulates, with improved stability also in the form of pharmaceutical composition thus allowing to increase the validity of the same.

It is clear to the person of ordinary skill in the art how these characteristics have a relevant industrial value.

With the aim to better illustrate the present invention, we give the following examples.

EXAMPLE 1

Preparation of mono-(2-ammonium-2-hydroxymethyl-1,3-propanediol) (2R,cis)-1,2-epoxypropyl-phosphonate (FT*) according to the present invention.

A) To a mixture of the bis-salt of THAM with Fosfomycin (10.3 g; 27.07 mmols), THAM (0.2 g; 1.65 mmols) and methanol (38 ml) methanesulphonic acid (2.6 g; 27.08 mmols) was added in 10 minutes. At the end of the addition the temperature of the mixture was 42°-43° C.

The mono-phenethylamine salt of Fosfomycin (7.5 g; 27.07 mmols) was then added while keeping the temperature at 42°-43° C. After a complete solution, ethanol (162 ml) was added by keeping the temperature at 42°-43° C. The mixture was then stirred according to the following parameters:

length of the anchor stirrer:diameter of the reactor=0.8;

applied power 0.15 kw/m$^3$ and a sample of FT (0.02 g) was seeded.

The mixture was slowly cooled at 0° C. in 3 hours and kept at that temperature for 3 hours.

The precipitate was filtered and washed with ethanol (10 ml). The wet product was mashed for 15 minutes with ethanol (25 ml) in the same reactor used before with the same stirring speed used for the crystallization.

The product was filtered, washed with ethanol (10 ml) and dried under vacuum at 50° C.

The desired product was thus obtained (10.5 g; 40.54 mmols, yield 75%, m.p.=122°-124° C.).

A sample of the product was subjected to the test for evaluating the surface area by using a Area Meter apparatus of Strooöhlein GmbH which uses the process of absorption of nitrogen at low temperatures according to the B.E.T. method [J. Am. Chem. Soc., 60, 309, (1938].

The test was replied three times thus obtaining the following values of surface area 0.37; 0.36 and 0.36 m$^2$/g.

A sample of the product was subjected to the test for the determination of the pH by using a digital pH-meter Top Tronic equipped with glass electrodes combined Metrohm code 6.0202.000. The apparatus was calibrated at 20° C. with solutions of known pH (pH 7 and pH 3).

An aqueous 5% solution of FT* kept at 20° C. showed pH 4.5.

B) The reaction described under point A was repeated 9 times, also on different scales, providing FT* having characteristics comprised in the following values of the parameters:

melting point: 122°-124° C.

surface area comprised between 0. and 0.5 m$^2$/g pH comprised between 4.0 and 5.0.

EXAMPLE 2

The present example concerns the preparation of FT (Ref. A) according to the procedure described in European Patent no. 0 27 597.

A) A solution of para-toluenesulphonic acid monohydrate (52.5 g; 275.19 mmols) in ethanol (260 ml) heated at 75° C. was added under stirring to a mixture of the bis salt of THAM with Fosfomycin (100 g; 262.88 mmols) and ethanol (660 ml) kept at 75° C.

By first a solution was obtained, then a crystalline solid begun to precipitate, and it was cooled under stirring in two hours at +3° C.

The precipitate was filtered under vacuum, washed with absolute ethanol (140 ml) at +10° C. and dried in oven under vacuum at 40° C.

FT was thus obtained (Ref. A) (53.7 g; 207.3 mmols, yield 78.9%, m.p. 114°-116° C.).

A sample was subjected to the tests for the evaluation of the surface area and pH according to the methods described in Example 1, with the following results: surface area: 1.72 m²/g (average of 3 tests), pH=3.77.

B) The reaction described under point A was repeated 4 times thus obtaining FT having characteristics comprised in the following values of the parameters:
melting point = 113°-116° C.
surface area comprised between 1.0 and 2.9 m²/g
pH comprised between 3.6 and 3.8.

EXAMPLE 3

The present example concerns the preparation of FT (Ref. B) according to the procedure described in Example 2 the Spanish patent no. 511,527.

A) After complete dissolution of a mixture of paratoluenesulphonic acid monohydrate (38.4 g; 201.87 mmols) methanol (400 ml) and THAM (23.8 g; 196,69 mmols), the mono-salts of phenethylamine with Fosfomycin (55.4 g; 200 mmols) was added.

The mixture was stirred at 30° C. up to complete dissolution, then isopropanol (1000 ml) was added and it was left under stirring for 1.5 hours at 20° C. The mixture was filtered and the precipitate was washed with a 1:1 mixture of methanol and isopropanol (200 ml).

The precipitate was dissolved in methanol (200 ml) at 55° C. Isopropanol (200 ml) was added under stirring and the mixture was cooled at room temperature in 1 hour and filtered. The insoluble was washed with a 1:1 mixture of methanol and isopropanol (100 ml).

The product was dried in oven at 50° C. under vacuum for 8 hours. FT (Ref. B) was thus obtained (39.1 g; 149.1 mmols, yield 74.6%, m.p. 120°-122° C.).

A sample of the product was subjected to the analysis for evaluating the surface area and the pH according to the methods described in Example 1, with the following results: surface area 0.88 m²/g (average of 3 tests), pH=3.8.

B) The reaction described under point A was repeated 4 times thus obtained FT with characteristics comprised between the following values of the parameters:
melting point =118°-122° C.
surface area comprised between 0.85 and 1.25 m²/g
pH comprised between 3.7 and 3.9.

EXAMPLE 4

Determination of the stability of FT rough material, comparison between FT*, Ref. A and Ref. B.

General procedure

About 11 g of each product was distributed into a crystallizer (glass crystallization vessel) having diameter of 13.5 cm so as to overlay its bottom with a ca. 0.5 cm layer.

The crystallizers were contempouraneously stored into a thermoclymatic room regulated at 25° C. and relative humidity (R.H.)=50±5% or in a room regulated at 25° C. and R.H.=70±5%.

Samples were withdrawn at the beginning of the test and after a pre-established time interval (24 hours for the samples stored at R.H.=50±5% and 6 hours for those stored at R.H.=70±5%).

The samples were analyzed to determine the titre in Fosfomycin according to the following procedures.

HPLC analysis according to the following chromatographic conditions:
apparatus Liquid Chromatograph Mod. 1081B equipped with refraction index detector and integrator Mod. 3880 both Hewlett Packard brand
column Nucleosil 10SB, 10 μm, 25 cm×4.6 mm i.d. Alltech brand
temperature of column 35° C. and of the detector 30° C.
eluent: 0.3M solution of $KH_2PO_4$
flow: 1 ml/min.

A standard FT solution was prepared by dissolving 500 mg of product in the eluent brought at 20 ml volume.

The product to be analyzed was dissolved in the eluent at 25 mg/ml concentration.

20 μl of standard solution and of solution to be analyzed were injected, the injections were repeated and the areas were averaged. In the above described conditions the retention time of Fosfomycin is ca. 6 minutes.

The percentage of FT in the sample (Ts) was determined by the following computation $$\frac{As}{Ar} \cdot \frac{Pr}{Ps} \cdot T(\%) = Ts(\%)$$

wherein
As=area corresponding to the analyzed solution
Ar=area corresponding to the reference standard solution
Pr=weight (in mg) of reference FT
Ps=weight (in mg) of the sample.
T(%)=percentage titre of FT in the reference standard.

The method affords a linear response inside the concentration interval 10-50 mg/ml.

The precision of the method for c=25 mg/ml is expressed by a variation coefficient (VC)=±0.94%.

The results are reported in the following table.

TABLE 1

| titre in Fosfomycin of the sample (initial titre = 100%) | | | |
|---|---|---|---|
| Conditions | Ref. A | Ref. B | FT* |
| 24 h, 25° C., 50 ± 5% RH | 93.93% | 96.84% | 98.84% |
| 6 h, 25° C., 70 ± 5% RH | 94.6% | 98.82% | 100% |

Drying rate of a granulate containing FT, comparison between FT*, Ref. A and Ref. B.

The industrial production of pharmaceutical compositions in granulate comprises a phase in which the active ingredient is granulated in the presence of water and a phase in which the granulate is dried under heating in order to reduce its content of water. In the case of active ingredients relatively unstable with respect to the humidity and heating, the drying phase can be very critical if protracted in time.

It is thus important, for a good processing of a relatively unstable active ingredient, that it could reach in a short time a sufficient degree of dryness.

Samples of FT*, Ref. A and Ref. B were granulated with water in amounts of 12% by weight.

At the end of the granulation process each sample contained water in amounts of 7% by weight.

For the preparation of the finished pharmaceutical form and for its stability it is necessary that the granulated FT contains water in amounts not higher than 0.3%.

The three granulated samples were thus dried at 50° C. and every 30 minutes samples were withdrawn for evaluating their water contents.

After 60 minutes the granulate prepared from FT* reached the acceptable water content (0.3%).

The granulates prepared from Ref. A and Ref. B, on the contrary, reached the water content of 0.3% after 210 minutes.

EXAMPLE 6

Stability of pharmaceutical forms in water soluble granulate, comparison between FT*, Ref. A and Ref. B.

Starting from the granulates obtained from FT*, Ref. A and Ref. B and dried up to a water content of 0.3% by weight, pharmaceutical compositions in hydrosoluble granulate were prepared according to the following procedure.

The sieved granulate was additioned with saccharin, orange and mandarin flavour and with saccharose.

After admixture, the ingredients were distributed in paper-polyethylene-aluminium-polyethylene bags, each one containing

| | |
|---|---|
| FT | 5.631 g |
| Saccharin | 0.016 g |
| Flavour | 0.140 g |
| Saccharose | 2.213 g |

For comparison purposes, bags prepared as above reported, starting from FT*, Ref. A and Ref. B were stored in a conditioned environment and periodically analyzed for ascertaining their stability. The analysis was performed by withdrawing the formulate from the bags, by grinding in a mortar and by weighing the amount equivalent to about 500 mg of FT which was transferred into a 20 ml volumetric flask and brought to volume by 0.3 m $KH_2PO_4$.

The reference solution was prepared by exactly weighing about 500 mg of reference FT and by dissolving in a 20 ml volumetric flask with the eluent solution.

An HPLC analysis was performed according to the procedure described in Example 4.

The precision of the method resulted to be 101.1% and is expressed by a variation coefficient (VC)= ±0.70%.

The storage conditions and the results are reported in the following table 2.

TABLE 2

| titre in Fosfomycin of water soluble granulates (initial titre = 100%) | | | |
|---|---|---|---|
| Storage conditions | Ref. A | Ref. B | FT* |
| 3 months, 40° C., 20% RH | 93.9% | 94.64% | 97.27% |
| 12 months, T and RH room values | 96.18% | 96.57% | 99.6% |
| 24 months, T and RH room values | — | 95.42% | 99.8% |

What we claimed is:

1. The mono-(2-ammonium-2-hydroxymethyl-1,3-propanediol)(2R, cis)-1,2-epoxypropyl-phosphonate having the following physico-chemical characteristics:
   melting point: 122°-124° C.
   ph: comprised between 4.0 and 5.0
   surface area: comprised between 0.2 and 0.5 $m^2/g$.

2. Mono-(2-ammonium-2-hydroxymethyl-1,3-propanediol)(2R, cis)-1,2-epoxypropyl-phosphonate prepared by steps consisting of:
   preparing in a reactor at a temperature between 15°-50° C., a methanolic solution of bis-(2-ammonium-2-hydroxymethyl-1,3-propanediol)(2R,cis)-1,2-epoxypropyl-phosphonate, equimolecular amounts of methanesulphonic acid, equimolecular amounts of mono (+)-alpha-phenethylammonium (2R,cis)-1,2-epoxypropyl-phosphonate and amounts of trihydroxymethyl-aminomethane (THAM) equal to 2-3% in moles with respect to the amount of THAM contained in the bis-salt of THAM with Fosfomycin;
   diluting the solution with ethanol in amounts comprised of between 4:1 and 10:1 with respect to the volume of the solution; and
   cooling the solution under slow stirring, wherein the ratio of a length of an anchor stirrer:diameter of the reactor is greater than 0.7 and the power is less than 0.25 kw/$m^3$.

3. A solid pharmaceutical composition containing as active ingredient the mono-(2-ammonium-2-hydroxymethyl-1,3-propanediol)-(2R,cis)-1,2-epoxypropyl-phosphonate having the following characteristics:
   melting point: 122°-124° C.
   pH: comprised between 4.0 and 5.0
   surface area: comprised between 0.2 and 0.5 $m^2/g$.

4. A solid pharmaceutical composition according to claim 3 in the form of water-soluble granulate.

5. A solid pharmaceutical composition containing the mono-(2-ammonium-2-hydroxymethyl-1,3-propanediol)(2R,cis)-1,2-epoxypropyl-phosphonate prepared according to the process steps of claim 2.

6. A solid pharmaceutical composition according to claim 5 in the form of water-soluble granulate.

* * * * *